(12) United States Patent
Ku (10) Patent No.: US 10,099,035 B2
(45) Date of Patent: Oct. 16, 2018

(54) ANTI-RESTERILIZATION COMPONENTS FOR CATHETER TREATMENT DEVICES AND ASSOCIATED DEVICES, SYSTEMS, AND METHODS

(71) Applicant: Medtronic Ardian Luxembourg S.a.r.l., Luxembourg (LU)

(72) Inventor: Vincent Ku, Palo Alto, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 179 days.

(21) Appl. No.: 15/123,224

(22) PCT Filed: Apr. 15, 2015

(86) PCT No.: PCT/US2015/026032
§ 371 (c)(1),
(2) Date: Sep. 1, 2016

(87) PCT Pub. No.: WO2015/164151
PCT Pub. Date: Oct. 29, 2015

(65) Prior Publication Data
US 2017/0143939 A1    May 25, 2017

Related U.S. Application Data

(60) Provisional application No. 61/982,472, filed on Apr. 22, 2014.

(51) Int. Cl.
| | |
|---|---|
| *A61M 25/00* | (2006.01) |
| *A61B 18/14* | (2006.01) |
| *A61L 2/20* | (2006.01) |
| *A61M 25/01* | (2006.01) |

(Continued)

(52) U.S. Cl.
CPC ..... *A61M 25/0097* (2013.01); *A61B 18/1492* (2013.01); *A61L 2/206* (2013.01); *A61M 25/00* (2013.01); *A61M 25/0136* (2013.01); *A61M 25/0147* (2013.01); *A61B 2017/0023* (2013.01); *A61B 2090/0814* (2016.02); *A61L 2202/24* (2013.01); *A61M 2205/273* (2013.01)

(58) Field of Classification Search
CPC .............. A61M 25/0097; A61M 25/00; A61M 25/0136; A61M 25/0147; A61M 2205/273; A61B 18/1492; A61B 2017/0023; A61B 2090/0814; A61L 2/206; A61L 2202/24

See application file for complete search history.

(56) References Cited

U.S. PATENT DOCUMENTS

2006/0025814 A1   2/2006 Hatori
2007/0197935 A1   8/2007 Reiley

FOREIGN PATENT DOCUMENTS

WO    WO98/37819 A1    9/1998

OTHER PUBLICATIONS

International Search Report, PCT/US2015/26032, dated Oct. 29, 2015, Applicant Medtronic Ardian Luxembourg S.A.R.L. , 3 pgs.

*Primary Examiner* — Michael C Miggins (57) ABSTRACT

Anti-resterilization components for medical devices, such as catheter assemblies, are disclosed herein. In one embodiment, for example, a catheter assembly comprises a handle assembly and an anti-resterilization component within the handle assembly. The anti-resterilization component comprises an absorptive material configured to absorb and selectively retain a component of a sterilization gas, such as ethylene oxide.

20 Claims, 3 Drawing Sheets

(51) Int. Cl.
*A61B 17/00* (2006.01)
*A61B 90/00* (2016.01)

ANTI-RESTERILIZATION COMPONENTS FOR CATHETER TREATMENT DEVICES AND ASSOCIATED DEVICES, SYSTEMS, AND METHODS

CROSS-REFERENCE TO RELATED APPLICATION(S)

This application claims the benefit of U.S. Provisional Patent Application No. 61/982,472 filed on Apr. 22, 2014, the disclosure of which is herein incorporated by reference in its entirety.

TECHNICAL FIELD

The present technology relates generally to anti-resterilization components for medical devices. In particular, various embodiments of the present technology are directed to anti-resterilization components for catheter treatment devices configured to discourage or prevent re-use of a medical device, such as a catheter treatment device.

BACKGROUND

Catheters are generally tubular medical devices configured for insertion into canals, vessels, passageways, lumens, or other suitable body cavities (e.g., to deliver energy to target tissue, to permit injection and/or withdrawal of fluids, to keep a passage open, etc.). Many advanced catheters are equipped with sophisticated therapeutic assemblies at distal end portions that are configured for delivery to various target treatment sites within the body. Such therapeutic assemblies are often intended for single use only in order to minimize risk of infection or other complications from inadequate subsequent sterilization(s). In practice, however, many medical devices are often re-sterilized after a first use and reused in a subsequent procedure. This practice can increase risk of infection and can introduce other complications to the patients, and can also reduce functionality of the medical device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

The present technology is directed to anti-resterilization components for medical devices. The medical devices described in this disclosure are configured to prevent or discourage sterilization after a first use (e.g., "resterilization"). The anti-resterilization components described herein can be incorporated into medical devices (e.g., within an interior cavity of a device, such as within a handle assembly, within cable assemblies, etc.). Sterilization of medical devices often includes use of a sterilizing gas, especially for devices that include delicate or steam-sensitive or heat-sensitive components, such as electronics, optics, paper, rubber and some plastics. Gaseous sterilization methods often employ ethylene oxide (hereinafter "EO"; also known as $C_2H_4O$; CAS #75-21-8, oxirane, epoxyethane, dimethylene oxide, or oxacylcopropane). Sterilization using EO is sometimes referred to as the "flexible chamber method," "gas diffusion sterilization," or "micro-dose sterilization." EO gas is introduced into the chamber in which a medical device is housed, saturates the atmosphere and perfuses all spaces (including tiny gaps inside the medical device) to kill any pathogens present in order to sterilize the devices. The process includes a degassing step, whereby residual EO is removed from the bag and vented. EO is a toxic gas, and thus high levels present in medical devices render the devices unsafe for use in a medical procedure. Typical flexible bag sterilization methods require 12 to 24 hours.

The disclosed anti-resterilization components are configured to increase the time required for the degassing step of such re-sterilization procedures. The anti-resterilization components are accordingly expected to render re-sterilization of medical devices inefficient, overly time-consuming, damaging to such devices, costly, and/or impossible. The anti-resterilization components, for example, may comprise an absorptive material configured to absorb and selectively retain a component of a sterilization gas (e.g., EO or a gas comprising EO) for an extended period of time (e.g., longer than other components of the medical device, at least one day, or at least about 14 days) after exposure of the medical device to the sterilization gas.

Specific details of several embodiments of the technology are described below with reference to FIGS. 1-3. Although various embodiments of medical devices are described herein with respect to catheter assemblies including anti-resterilization components, it will be appreciated that the disclosed technology may also be used for other types of medical devices, particularly those that are intended to be used one time only (e.g., single-use or disposable medical devices). Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-3.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device. The headings provided herein are for convenience only and should not be construed as limiting the subject matter disclosed.

I. CATHETER ASSEMBLIES INCLUDING ANTI-RESTERILIZATION COMPONENTS

Figure 1:
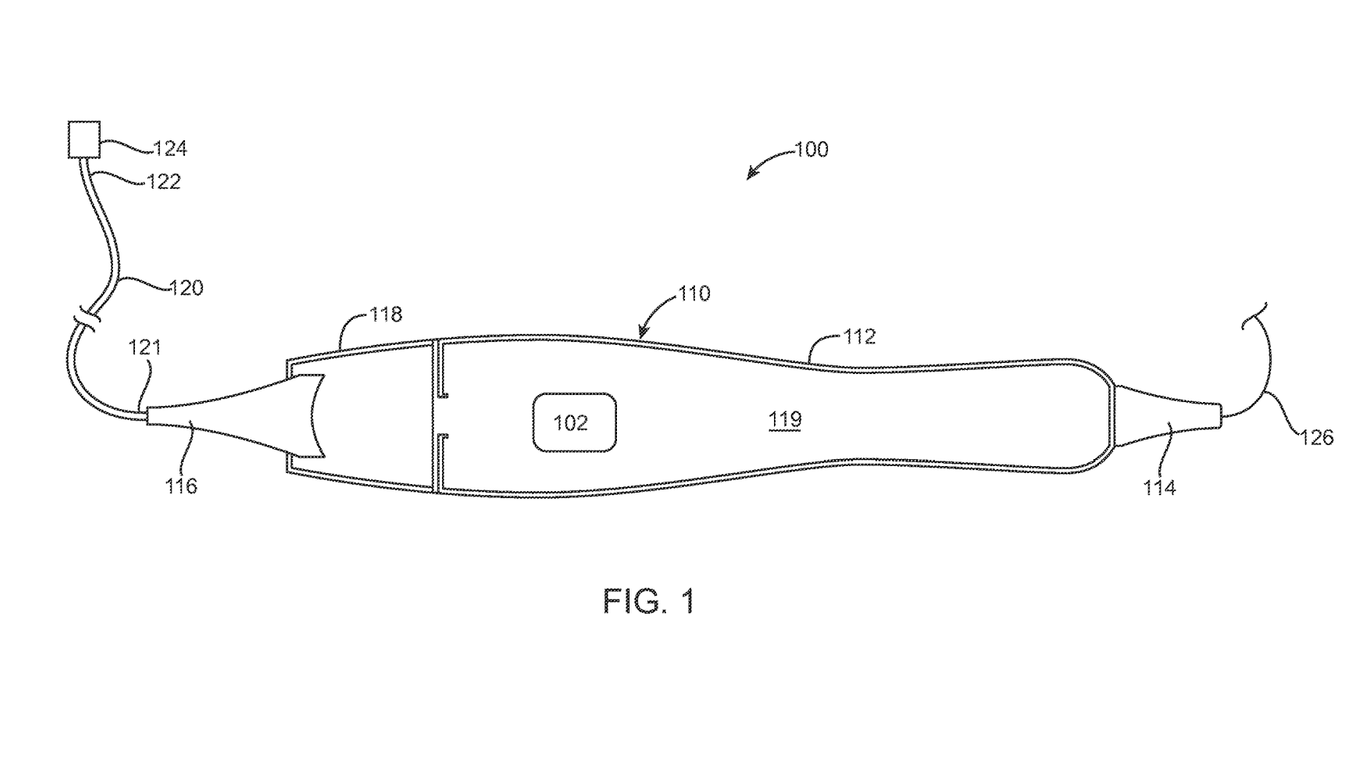
FIG. 1 is a cross-sectional view of a catheter assembly including an anti-resterilization component configured in accordance with an embodiment of the present technology.

FIG. 1 is a cross-sectional view of a catheter assembly 100 including an anti-resterilization/anti-reuse component 102 (shown schematically) configured in accordance with an embodiment of the present technology. As described in more detail below, the anti-resterilization component 102 comprises an absorptive material configured to absorb and selectively retain one or more sterilization gases (e.g., EO gas) during a sterilization process. In some embodiments, for example, the anti-resterilization component 102 absorbs a sterilization gas and is configured to retain the sterilization gas longer or substantially longer than other components of the catheter assembly 100 during a degassing process. In this way, the anti-resterilization component 102 is configured to render re-sterilization of the catheter assembly 100 inefficient, time-consuming, inconvenient, or otherwise deleterious to the catheter assembly and/or any one or more of its component parts. In some embodiments, for example, the anti-resterilization component 102 is configured to selectively retain the sterilization gas (e.g., EO gas) or a component thereof at least one day (e.g., about one day, about two days, etc. up to an including 14 days) after exposure of the catheter assembly 100 and corresponding anti-resterilization component 102 to the sterilization gas. Further details regarding the anti-resterilization component 102 are described below.

The catheter assembly 100 includes a handle assembly 110 having a housing 112, a proximal strain relief portion 114, a distal strain relief portion 116, and an optional rotator 118. The housing 112 defines a cavity 119 containing the anti-resterilization component 102. The catheter assembly 100 also includes a flexible, elongated tubular shaft 120 carried by and extending from the handle assembly 110. The shaft 120 has a proximal portion 121 at the handle assembly 110 and a distal portion 122 configured to intravascularly locate a distal therapeutic assembly 124 at a treatment location within a body lumen, such as a suitable blood vessel, duct, airway, or other naturally occurring lumen within the human body. The therapeutic assembly 124, for example, can be configured to provide or support therapy (e.g., a neuromodulation treatment) at the treatment location.

The catheter assembly 100 may be operably coupled to a console (not shown) via a cable 126 extending from the proximal strain relief portion 114 of the handle assembly 110. The cable 126 may be either removably attached (e.g., via a plug or other cable connector) or permanently attached (e.g., via adhesives and/or solder) to the handle assembly 110. Optionally, the cable 126 may comprise a rotational electrical coupling that facilitates independent rotation of the handle assembly 110 relative to the cable 126.

The console (not shown) can be configured to control, monitor, supply energy, and/or otherwise support operation of the catheter assembly 100. When the catheter assembly 100 is configured for electrode-based, heat-element-based, or transducer-based treatment, for example, the console may include an energy generator configured to generate radio frequency (RF) energy (e.g., monopolar and/or bipolar RF energy), pulsed electrical energy, microwave energy, optical energy, ultrasound energy (e.g., intravascularly delivered ultrasound energy, high-intensity focused ultrasound energy), direct heat, radiation (e.g., infrared, visible, and/or gamma radiation), and/or another suitable type of energy. Similarly, when the catheter assembly 100 is configured for chemical-based treatment (e.g., drug infusion), the console can include a chemical reservoir (not shown) and can be configured to supply the catheter with one or more chemicals. Alternatively, in some embodiments the catheter assembly 100 may be self-contained or otherwise configured for operation without connection to a console.

In some embodiments, the anti-resterilization component 102 may comprise, consist of, or consist essentially of polyvinyl chloride (PVC). In other embodiments, the anti-resterilization component 102 may comprise, consist of, or consist essentially of a polyether urethane thermoplastic. In still further embodiments, the anti-resterilization component 102 comprises, consists of, or consists essentially of a polyether urethane thermoplastic and blue polyethylene master batch (PEMB). For example, the PEMB may be present in an amount of about 0.1% by weight to about 10% by weight, compared to the weight of the polyether urethane thermoplastic, such as 0.1% by weight, 0.2% by weight, 0.3% by weight, 0.4% by weight, 0.5% by weight, 0.6% by weight, 0.7% by weight, 0.8% by weight, 0.9% by weight, 1% by weight, 1.1% by weight, 1.2% by weight, 1.3% by weight, 1.4% by weight, 1.5% by weight, 1.6% by weight, 1.7% by weight, 1.8% by weight, 1.9% by weight, 2% by weight, 2.1% by weight, 2.2% by weight, 2.3% by weight, 2.4% by weight, 2.5% by weight, 2.6% by weight, 2.7% by weight, 2.8% by weight, 2.9% by weight, 3% by weight, 4% by weight, 5% by weight, 6% by weight, 7% by weight, 8% by weight, 9% by weight, or 10% by weight, compared to the weight of the polyether urethane thermoplastic. In one particular embodiment, the PEMB is present in an amount of about 2% by weight, compared to the weight of the polyether urethane thermoplastic. In still other embodiments, the PEMB comprises, consists of, or consists essentially of low density polyethylene (LDPE), titanium dioxide and phthalocyanine blue (e.g., CAS #147-14-8).

In still further embodiments, the anti-resterilization component 102 may comprise, consist of, or consist essentially of a high density polymer. The high density polymer can include, for example, a high density polymer foam such as an open-cell or a closed-cell foam. In other embodiments, the anti-resterilization component 102 may comprise, consist of, or consist essentially of a porous ceramic material. The porous ceramic material can include, for example, a low density reticulated ceramic having any one or more of the following: low thermal conductivity, low dielectric constant, high thermal shock resistance, high specific strength, and/or high chemical resistance. In some embodiments, the porous ceramic material can include an oxide ceramic, such as an alumina and/or a zirconia. In still other embodiments, the porous ceramic material includes a non-oxide ceramic, such as a carbide, a boride, a nitride and/or a silicide. The porous ceramic material may be in any suitable shape or configuration including, for example, a foam, a honeycomb, interconnected rods, fibers, or hollow spheres.

In still further embodiments, the anti-resterilization component 102 comprises, consists of, or consists essentially of a powdered sintered metal. In some embodiments, for example, the powdered sintered metal is formed by compacting the powdered metal component(s) into a suitable mold or die and placing the material under high heat for a period of time sufficient to bond the particles. In another embodiment, the powdered sintered material is formed by applying an electrical current to the powdered metal component(s) to induce bonding.

In some embodiments, the anti-resterilization component 102 (or at least a portion thereof) may be formed in the shape of a microtube. The microtube, for example, can be incorporated into any suitable feature of the catheter assembly 100. For example, the microtube can be used as conduit for any wire or cable component of the catheter assembly 100. Alternatively or in addition, the microtube can be a separate component of the catheter assembly 100 and can be in any configuration suitable for incorporation with the assembly, such as a bundle of microtubes, or a microtube tangled like a hair ball that is capable of being placed inside (e.g., secured or unsecured) the handle assembly 110, the proximal strain relief portion 114, the distal strain relief portion 116, the shaft 120, the proximal portion 121 of the shaft 16, and/or the cable 126. Incorporating the anti-resterilization component 102 into an existing structure of the catheter assembly 100, for example, may further reduce the ability for an unauthorized user to remove the anti-resterilization component 102 from the catheter assembly 100 before a second (or subsequent) sterilization process.

In other embodiments, the anti-resterilization component 102 may be positioned in a balloon (not shown) carried within the handle assembly 110. In such embodiments, the balloon may include an array of apertures/openings positioned to selectively allow egress of one or more sterilization gases (e.g., EO). The balloon, for example, may further increase the time required for the degassing process.

Although the anti-resterilization component 102 is shown schematically in FIG. 1, it will be appreciated that the anti-resterilization component 102 may have a variety of suitable shapes/sizes/configurations. In some embodiments, for example, at least a portion of the anti-resterilization component 102 is in the shape of a sponge. As used herein, the term "sponge" refers generally to a material having a plurality of holes or channels into which a gas may permeate. In other embodiments, at least a portion of the anti-resterilization component 102 may be shaped like wool. As used herein, the term "wool" refers generally to a material comprising a plurality of hair-like fibers, optionally interwoven or otherwise configured into a continuous or contiguous mass. In still other embodiments, at least a portion of the anti-resterilization component 102 may shaped into a thin flexible sheet of material, such as fabric. In further embodiments, the anti-resterilization component 102 may have a variety of other suitable shapes/configurations.

Figures 2A, 2B:
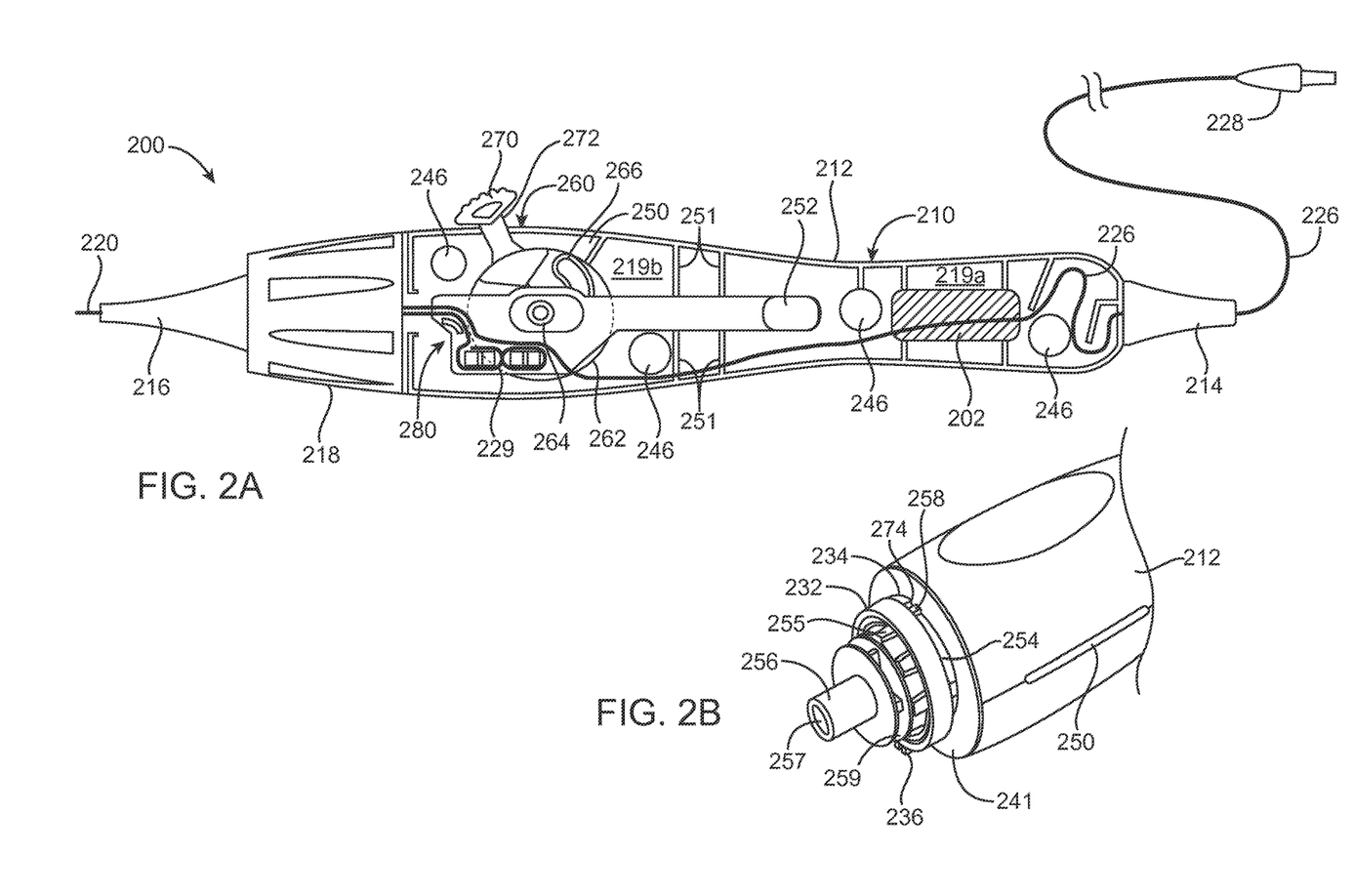
FIG. 2A is a cross-sectional view of a catheter assembly including an anti-resterilization component configured in accordance with another embodiment of the present technology.
FIG. 2B is an isometric view of a front portion of the catheter assembly of FIG. 2A.

FIG. 2A is a cross-sectional view of a portion of a catheter assembly 200 including an anti-resterilization/anti-reuse component 202 configured in accordance with another embodiment of the present technology. The anti-resterilization component 202, for example, can be identical or similar to the anti-resterilization component 102 described above with reference to FIG. 1, and can have many of the same features as the anti-resterilization component 102. For example, as with the anti-resterilization component 102 described above, the anti-resterilization component 202 comprises a material adapted to absorb and selectively retain one or more sterilization gases (e.g., EO gas) to render re-sterilization of the catheter assembly 200 impracticable.

In the illustrated embodiment, the catheter assembly 200 includes a handle assembly 210 and an elongated shaft 220 extending from the handle assembly 210. The handle assembly 210 includes a housing 212, a proximal strain relief portion 214, a distal strain relief portion 216, a rotator 218, an actuator assembly 260, and a carrier 280. The catheter assembly 200 may additionally include a cable 226 having a plug or other cable connector 228 at a distal end portion of the cable 226. The catheter assembly 200 may be operably coupled to a console (not shown) via the cable 226 and corresponding plug 228. The console, for example, may be generally similar to the console(s) described above with reference to FIG. 1.

The housing 212 defines one or more internal cavities 219a and 219b. In some embodiments, internal cavities 219a-b are defined by additional internal components or features of the housing assembly 212, such as mating feature(s) 246, one or more channels 251, longitudinal channel(s) 252, fins, ribs, and the like. A control wire 229 extends the length of the elongated shaft 220 and into the handle assembly 210. The control wire 229 further extends between the carrier 280 and a proximal portion of the handle assembly 210.

By rotating the actuator assembly 260 proximally, the caregiver (not shown) may proximally translate the carrier 280 relative to the housing assembly 212 in order to proximally retract the control wire 229 relative to the elongated shaft 220 (and thereby selectively manipulate the shaft 220 during therapy). Actuator assembly 260 comprises an actuator body 262 having a pivot 264 and a cam 266. The cam 266 is positioned on a surface of the actuator facing an upper portion of the housing 212 and carrier 280 in the assembled configuration.

The actuator assembly 260 also has as an actuator button 270 coupled to the actuator body 262 via an actuator button arm 272. The actuator button arm 272 acts as a lever arm, providing additional torque and mechanical advantage during rotation of the actuator assembly 260. The actuator button 270 optionally has a larger width than the actuator button arm 272 to facilitate tactile manipulation and ergonomic handling of the actuator button 270 by a caregiver. The actuator button 270 initially is positioned in a forward or distal position relative to housing assembly 212 (as shown in FIG. 2A). The caregiver may pull back (i.e. proximally) on the button 270 to proximally rotate the actuator 260 relative to the housing assembly 212. The range of distances separating the actuator button 270 from the rotator 218 during caregiver manipulation of the handle assembly 210 is specified in a manner that facilitates single-handed ergonomic use of the catheter assembly 200, even when the actuator button 270 is positioned in its proximal-most or distal-most position relative to the housing assembly 212.

Upon mating of the upper housing portion and the lower housing portion to form the housing assembly 212, the actuator button arm 272 of the actuator 260 is seated within an actuator channel 250 formed through mating of the upper and lower housings (see FIG. 2B). Actuator channel 250 provides the caregiver with access to the actuator button 270 from outside the housing assembly 212, allowing the caregiver to rotate the actuator 260 relative to the housing assembly via the actuator button 270 while the actuator body 262 is disposed within the housing assembly 212. The carrier 280 is also positioned within the housing assembly 212. The carrier 280 is configured to interact with the actuator 260 and the housing assembly 212 to transform rotation of the actuator 260 into translation of the carrier 280 relative to the housing assembly 212, and thereby translation of the control wire 229 relative to the elongated shaft 220.

As noted above, the anti-resterilization component 202 may be carried within the housing 212 of the handle assembly 210. In one embodiment, for example, the anti-resterilization component 202 is located inside the internal cavity 219a. In some embodiments, the anti-resterilization component 202 may be secured to an inner surface of the housing 212 using, for example, a fastener, adhesive, friction, tension, and/or a combination thereof. In other embodiments, the anti-resterilization component 202 may be incorporated into an inner surface of the housing 212 (e.g., as a coating, film, layer, veneer, or a combination thereof). In some embodiments, the anti-resterilization component 202 may be incorporated into one or more features of the housing 212 such as, for example, the mating feature(s) 246, one or more channels 251, longitudinal channel(s) 252, fins, ribs, distal strain relief portion 216, proximal strain relief portion 214, the rotator 218, the actuator 260, the carrier 280, and/or a combination thereof. In still other embodiments, the anti-resterilization component 202 may have a different arrangement and/or configuration within the handle assembly 210.

FIG. 2B is an isometric view of a front portion of the catheter assembly 200 of FIG. 2A. As best seen in FIG. 2B, a rotational limiting assembly may optionally be provided to limit independent rotation of the elongated shaft 220 relative to the handle assembly 210. In such embodiments, interactions of the rotator 218, an outer limiter ring 232, and an inner limiter ring 234 facilitate independent rotation of the elongated shaft 220 relative to the handle assembly 210, while providing a rotational limiting assembly that limits such independent rotation, thereby reducing a risk of control and/or supply wire entanglement or breakage. These interactions are described in more detail below.

The inner limiter ring 234 is positioned concentrically over a distal portion of the housing assembly 212, the outer limiter ring 232 is positioned concentrically over the inner limiter ring 234, and the rotator 218 (FIG. 2A) is positioned concentrically over the outer limiter ring 232. The distal portion of the housing assembly 212 comprises cylindrical segment 254 about which the inner limiter ring 234 is concentrically positioned. The cylindrical segment 254 is of reduced diameter relative to a surface 241 of the housing assembly 212 just proximal of the cylindrical segment 254, such that proximal surfaces of the inner limiter ring 234, the outer limiter ring 232, and the rotator 218 (FIG. 2A) abut surface 241 of the housing assembly 212. These abutments may constrain proximal translation of the inner limiter ring 234, the outer limiter ring 232 and/or the rotator 218 relative to the housing assembly 212.

An inner diameter of the inner limiter ring 234 may be just slightly greater than an outer diameter of the cylindrical segment 254, such that the inner limiter ring 234 may rotate concentrically about the cylindrical segment 254. Likewise, an inner diameter of an outer cylindrical segment of the outer limiter ring 232 is just slightly greater that an outer diameter of an inner cylindrical segment of the inner limiter ring 234, such that the outer limiter ring 232 may rotate concentrically about the inner limiter ring 234. Finally, an inner diameter of a proximal region of the rotator 218 is just slightly greater than an outermost diameter of the outer limiter ring 232 at an outer tab 236, such that the rotator 218 may rotate concentrically about the outer limiter ring 232.

Referring to FIGS. 2A and 2B together, the geometric configuration of handle assembly 210 facilitates independent rotation of the rotator 218 relative to the housing assembly 212, while constraining longitudinal translation of the rotator 218 relative to the housing assembly 212. Via its connection to the rotator, the elongated shaft 220 likewise may be rotated without rotating the handle assembly 210 (i.e., without rotating the housing assembly 212), while translation of the handle assembly 210 also translates the elongated shaft 220. The distal portion of the housing assembly 212 comprises housing shaft 256 (located distally and of reduced cross-section relative to the housing assembly's cylindrical segment 254) having lumen 257. The rotator 218 comprises a rotator shaft (not shown) having a lumen configured to be positioned within the lumen 257 of the housing shaft 256 when the rotator 218 is attached to the housing assembly 212 to facilitate independent rotation of the rotator 218 relative to the housing assembly 212.

The rotator 218 optionally may comprise one or more rotator elements (not shown) that engage or rub against cylindrical segment 254 of housing assembly 212 to provide tactile feedback to the caregiver during rotation of the rotator 218 relative to the housing assembly 212. In some embodiments, for example, all or a portion of the cylindrical segment 254 optionally may comprise a surface pattern or engagement features 255 that interact with the rotator elements to provide such tactile feedback. For example, the surface pattern 255 may comprise alternating segments where the radius of cylindrical segment 254 is slightly increased then decreased. As the caregiver rotates the rotator 218, resistance slightly increases while the rotator elements traverse the increased diameter segments and slightly decreases while the rotator elements traverse the decreased diameter segments. These alternating segments of the surface pattern 255 may traverse known angular segments about the circumference of the cylindrical segment 254. The caregiver may monitor the tactile feedback provided during rotation of the rotator elements about the alternating segments of the surface pattern 255 to monitor the degree of angular rotation of the cable 226. In one embodiment, the surface pattern 255 provides tactile feedback (e.g., transitions between alternating segments of increased and decreased diameter) every 45 degrees of relative rotation between the housing assembly 212 and the rotator 218. It will be appreciated, however, that such tactile feedback alternatively may be provided at any other desired degree of relative rotation.

The rotator elements additionally or alternatively may abut and constrain distal translation of the inner limiter ring 234 and/or outer limiter ring 232 relative to the rotator 218, thereby limiting distal translation of the housing assembly 212 relative to the rotator 218. Translation of the housing assembly 212 relative to the rotator 218 additionally or alternatively may be constrained via engagement elements that extend radially inward from the rotator elements and sit within reduced diameter cylindrical channel 259 of the housing assembly's cylindrical segment 254. The engagement elements, for example, may comprise one-way valves that allow the rotator 218 to be press fit over the housing assembly 212 with the engagement elements locking into position within the cylindrical channel 259. The engagement elements facilitate rotation of the rotator 218 relative to the housing assembly 212 while constraining proximal (and optionally distal) translation of the housing assembly 212 relative to the rotator 218.

Rotation of the elongated shaft 220 relative to the handle assembly 210 may be limited in a variety of ways, e.g., may be limited to a predetermined or optimal number of rotations of the elongated shaft 220 relative to the handle assembly 210 in a variety of ways. In FIG. 2B, for example, elongated shaft rotation limitation is achieved via housing nub 258 disposed on cylindrical segment 254 and abutting surface 241 of the housing assembly 212 via inner arc tab 274 of inner limiter ring 234 that extends both radially outward and longitudinally proximal of the inner cylindrical segment of the inner limiter ring 234, via outer tab 236 of outer limiter ring 232 that extends radially outward and longitudinally along the length as well as proximal of the outer cylindrical segment of the outer limiter ring 232, and via a rotator tab (not shown) that extends radially inward from an inner wall of rotator 218 at or near a proximal end of the rotator 218.

Caregiver rotation of the rotator 218 relative to the housing assembly 212 may cause (a) the rotator tab to abut outer tab 236, limiting further rotation of the rotator relative to the outer limiter ring 232; (b) the outer tab 236 to abut the inner arc tab 274, limiting further rotation of the outer limiter ring 232 relative to the inner limiter ring 234; and (c) the inner arc tab 274 to about the housing nub 258, limiting further rotation of the inner limiter ring 234 relative to the housing assembly 212, and thereby limit further rotation of the rotator 218 relative to the housing assembly 212. As the elongated shaft 220 is coupled to the rotator 218, rotation of the elongated shaft 220 relative to the handle assembly 210 is thus also limited to a predetermined or optimal number of rotations of the elongated shaft 220 relative to the handle assembly. Further details regarding the catheter assembly 200 may be found in U.S. patent application Ser. No. 12/759,641, filed Apr. 13, 2010, and incorporated herein by reference in its entirety.

Figure 3:
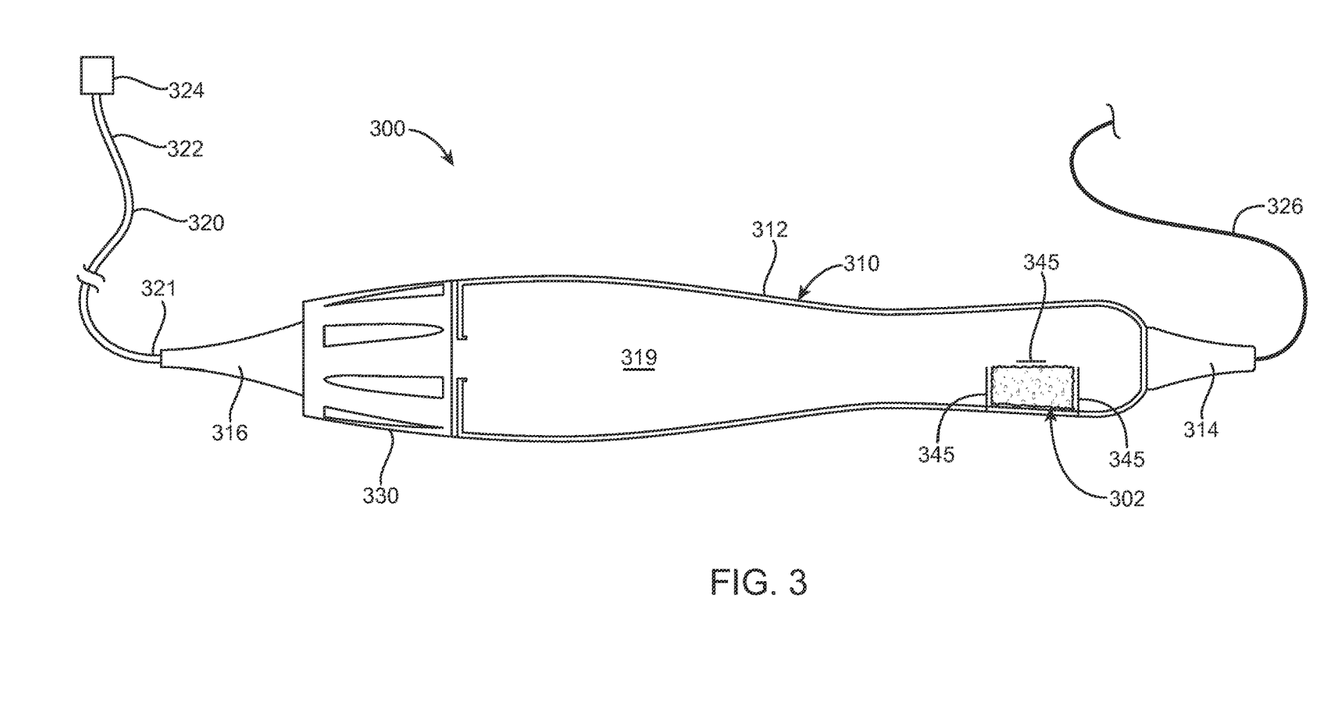
FIG. 3 is a cross-sectional view of a catheter apparatus including an anti-resterilization component configured in accordance with still another embodiment of the present technology.

FIG. 3 is a cross-sectional view of a catheter apparatus 300 configured in accordance with still another embodiment of the present technology. The catheter apparatus 300 may have a number of features generally similar to the catheter assemblies 100/200 described above with reference to FIGS. 1-2B. For example, the catheter apparatus 300 comprises a handle 310, an elongated tubular shaft 320 having a proximal portion 321 and a distal portion 322, and a treatment assembly/therapeutic assembly 324 at the distal portion 322 of the elongated shaft 320. In some embodiments, the catheter apparatus 300 may include a distal strain relief portion 316 that protects a connection between the proximal portion 321 of the shaft 320 and the handle 310.

The catheter apparatus 300 further includes means for preventing resterilization 302. The means for preventing resterilization 302 is adapted to absorb and selectively retain one or more sterilization gases (e.g., EO gas). The means for preventing resterilization 302, for example, may have a number of features identical to or generally similar to the features of anti-resterilization components 102 and 202 described above with reference to FIGS. 1-2B. The handle 310 of the catheter apparatus 300 includes a housing 312 defining an inner cavity 319 in which the means for preventing resterilization 302 is located. The means for preventing resterilization 302 can be unsecured or, alternatively, may be secured within the cavity 319 by any suitable means. For example, as shown in FIG. 3, the means for preventing resterilization 302 may be secured within one or more ridges 345 of the housing 312. In some embodiments, for example, the ridges 345 may be continuous or contiguous with an inner wall of the housing 312. For example, the ridges 345 may be integrally formed with the housing 312 and composed of the same material as the housing 312. In other embodiments, however, the ridges 345 may be separate components that are attached to the housing 312 and may have different features and/or configurations.

The catheter apparatus 300 may be operably coupled to a console (not shown) via a cable 326 extending from a proximal strain relief portion 314 of the handle 310. As with the cable 126, the cable 326 may be either removably attached (e.g., via a plug or other cable connector) or permanently attached (e.g., via adhesives and/or solder) to the handle 310. The console (not shown) can be configured to control, monitor, supply energy, and/or otherwise support operation of the catheter apparatus 300 and its corresponding treatment assembly 324.

Although much of the disclosure in this Specification relates to catheters or components thereof, the apparatuses, methods and systems described herein may also be used in association with other medical devices. For example, any medical device which must be sterilized, but is intended for only a single use, may include an anti-resterilization component as described herein. Accordingly, a person of skill in the art will recognize that the anti-resterilization components disclosed herein in connection with a catheter may also be incorporated for use in any other medical device without deviating from the scope of the present technology.

II. EXAMPLES

The following examples are illustrative of several embodiments of the present technology:

1. A catheter assembly, comprising:
  a handle assembly;
  an elongated tubular shaft having a proximal portion at the handle assembly and a distal portion;
  a therapeutic assembly at the distal portion of the elongated shaft and adapted to be located at a target location within a blood vessel of a human patient; and
  an anti-resterilization component within the handle assembly, wherein the anti-resterilization component comprises an absorptive material configured to absorb and selectively retain ethylene oxide (EO) gas.
2. The catheter assembly of example 1 wherein the absorptive material is polyvinyl chloride (PVC).
3. The catheter assembly of example 1 wherein the absorptive material is a polyether urethane thermoplastic.
4. The catheter assembly of example 2 or example 3 wherein the absorptive material further comprises blue polyethylene master batch (PEMB).
5. The catheter assembly of example 4 wherein the PEMB is 2% loading by weight.
6. The catheter assembly of example 1 wherein the absorptive material is polyvinyl chloride (PVC), and wherein the absorptive material is configured to selectively retain EO gas for at least 14 days after exposure of the catheter assembly to the EO gas.
7. The catheter assembly of example 1 wherein the anti-resterilization component is composed of a high density polymer.
8. The catheter assembly of example 1 wherein the anti-resterilization component is composed of a porous ceramic material.
9. The catheter assembly of example 1 wherein the anti-resterilization component is composed of a powdered sintered metal.
10. The catheter assembly of any one of examples 1 to 9 wherein the anti-resterilization component comprises a microtube positioned within the handle assembly.
11. The catheter assembly of example 10 wherein the microtube is preshaped into a sponge-like shape.
12. The catheter assembly of any one of examples 1 to 9 wherein the anti-resterilization component has a sponge-like shape and is positioned within the handle assembly.
13. The catheter assembly of any one of examples 1 to 12 wherein the absorptive material is configured to absorb and selectively retain the EO gas during a sterilization and degassing process, and wherein the absorptive material retains the EO gas for a period of time longer than the other components of the catheter assembly.
14. The catheter assembly of any one of examples 1 to 13 wherein the anti-resterilization component is positioned within a balloon carried by the handle assembly, and wherein the balloon comprises an array of openings positioned to selectively allow egress of EO gas.
15. A handle assembly, comprising:
  a housing;
  a rotator coupled to a proximal region of an elongated flexible shaft extending rotatably along an axis and having a deflectable distal region configured for intravascular delivery to a blood vessel, wherein the rotator is configured to rotate the entire elongated flexible shaft through the proximal region without rotating the housing;

an actuator operatively connected to the deflectable distal region of the elongated flexible shaft; and an anti-reuse component carried within the housing, wherein the anti-reuse component comprises a material adapted to absorb and selectively retain ethylene oxide (EO) gas;

wherein the actuator is configured to deflect the deflectable distal region of the elongated flexible shaft, and wherein the actuator is operatively connected to a control wire that extends within a lumen of the elongated flexible shaft from the handle assembly to the deflectable distal region, and wherein the handle assembly comprises a rotational limiting assembly configured to prevent rotation of the elongated flexible shaft and the rotator beyond a predetermined number of rotations.

16. The handle assembly of example 15 wherein the anti-reuse component is composed of polyvinyl chloride (PVC).

17. The handle assembly of example 15 or example 16 wherein the anti-reuse component is configured to selectively retain EO gas for at least 14 days after exposure of the handle assembly to the EO gas.

18. The handle assembly of example 15 wherein the anti-reuse component is composed of a polyether urethane thermoplastic with 2% loading by weight of blue polyethylene master batch (PEMB).

19. The handle assembly of example 15 wherein the anti-reuse component is composed of at least one of the following: a porous ceramic, a high density polymer foam, or a powder sintered metal.

20. A catheter apparatus, comprising:

a handle;

an elongated tubular shaft having a proximal portion coupled to the handle and a distal portion;

a treatment assembly at the distal portion of the elongated shaft and shaped and sized to be intravascularly positioned at a target location within a blood vessel of a human patient; and means for preventing resterilization of the catheter, wherein the means for preventing resterilization is adapted to absorb and selectively retain ethylene oxide (EC)) gas.

III. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, the medical devices and catheter assemblies described herein may be used with catheters having therapeutic assemblies with a variety of different configurations (e.g., single electrode, expandable basket, expandable balloon, one or more transducers, etc.). Further, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A catheter assembly, comprising:

a handle assembly;

an elongated tubular shaft having a proximal portion at the handle assembly and a distal portion;

a therapeutic assembly at the distal portion of the elongated shaft and adapted to be located at a target location within a blood vessel of a human patient; and an anti-resterilization component within the handle assembly, wherein the anti-resterilization component comprises an absorptive material configured to absorb and selectively retain ethylene oxide (EO) gas.

2. The catheter assembly of claim 1 wherein the absorptive material is polyvinyl chloride (PVC).

3. The catheter assembly of claim 1 wherein the absorptive material is polyvinyl chloride (PVC), and wherein the absorptive material is configured to selectively retain EO gas for at least 14 days after exposure of the catheter assembly to the EO gas.

4. The catheter assembly of claim 1 wherein the anti-resterilization component is composed of a high density polymer.

5. The catheter assembly of claim 1 wherein the anti-resterilization component is composed of a porous ceramic material.

6. The catheter assembly of claim 1 wherein the anti-resterilization component is composed of a powdered sintered metal.

7. The catheter assembly of claim 1 wherein the anti-resterilization component has a sponge-like shape and is positioned within the handle assembly.

8. The catheter assembly of claim 1 wherein the absorptive material is configured to absorb and selectively retain the EO gas during a sterilization and degassing process, and wherein the absorptive material retains the EO gas for a period of time longer than the other components of the catheter assembly.

9. The catheter assembly of claim 1 wherein the anti-resterilization component is positioned within a balloon carried by the handle assembly, and wherein the balloon comprises an array of openings positioned to selectively allow egress of EO gas.

10. The catheter assembly of claim 1 wherein the absorptive material is a polyether urethane thermoplastic.

11. The catheter assembly of claim 10 wherein the absorptive material further comprises blue polyethylene master batch (PEMB).

12. The catheter assembly of claim 11 wherein the PEMB is 2% loading by weight.

13. The catheter assembly of claim 1 wherein the anti-resterilization component comprises a microtube positioned within the handle assembly.

14. The catheter assembly of claim 13 wherein the microtube is preshaped into a sponge-like shape.

15. A handle assembly, comprising:
- a housing;
- a rotator coupled to a proximal region of an elongated flexible shaft extending rotatably along an axis and having a deflectable distal region configured for intravascular delivery to a blood vessel, wherein the rotator is configured to rotate the entire elongated flexible shaft through the proximal region without rotating the housing;
- an actuator operatively connected to the deflectable distal region of the elongated flexible shaft; and
- an anti-reuse component carried within the housing, wherein the anti-reuse component comprises a material adapted to absorb and selectively retain ethylene oxide (EO) gas;
- wherein the actuator is configured to deflect the deflectable distal region of the elongated flexible shaft, and wherein the actuator is operatively connected to a control wire that extends within a lumen of the elongated flexible shaft from the handle assembly to the deflectable distal region, and
- wherein the handle assembly comprises a rotational limiting assembly configured to prevent rotation of the elongated flexible shaft and the rotator beyond a predetermined number of rotations.

16. The handle assembly of claim 15 wherein the anti-reuse component is composed of a polyether urethane thermoplastic with 2% loading by weight of blue polyethylene master batch (PEMB).

17. The handle assembly of claim 15 wherein the anti-reuse component is composed of at least one of the following: a porous ceramic, a high density polymer foam, or a powder sintered metal.

18. The handle assembly of claim 15 wherein the anti-reuse component is composed of polyvinyl chloride (PVC).

19. The handle assembly of claim 18 wherein the anti-reuse component is configured to selectively retain EO gas for at least 14 days after exposure of the handle assembly to the EO gas.

20. A catheter apparatus, comprising:
- a handle;
- an elongated tubular shaft having a proximal portion coupled to the handle and a distal portion;
- a treatment assembly at the distal portion of the elongated shaft and shaped and sized to be intravascularly positioned at a target location within a blood vessel of a human patient; and
- means for preventing resterilization of the catheter, wherein the means for preventing resterilization is adapted to absorb and selectively retain ethylene oxide (EO) gas.

* * * * *